(12) United States Patent
Baubeau (10) Patent No.: US 11,504,277 B2
(45) Date of Patent: Nov. 22, 2022

(54) APPARATUS FOR TREATING A TISSUE, INCLUDING ORIGINAL OPTICAL SYSTEMS OF DEFLECTION AND FOCUSING OF A LASER BEAM

(71) Applicant: KERANOVA, Saint Etienne (FR)

(72) Inventor: Emmanuel Baubeau, Saint Etienne (FR)

(73) Assignee: KERANOVA, Saint Etienne (FR)

( * ) Notice: Subject to any disclaimer, the term of this patent is extended or adjusted under 35 U.S.C. 154(b) by 0 days.

(21) Appl. No.: 17/045,231

(22) PCT Filed: Apr. 5, 2019

(86) PCT No.: PCT/EP2019/058627
§ 371 (c)(1),
(2) Date: Oct. 5, 2020

(87) PCT Pub. No.: WO2019/193148
PCT Pub. Date: Oct. 10, 2019

(65) Prior Publication Data
US 2021/0161708 A1     Jun. 3, 2021

(30) Foreign Application Priority Data
Apr. 6, 2018   (FR) ...................................... 1870407

(51) Int. Cl.
*A61F 9/008*        (2006.01)
(52) U.S. Cl.
CPC ........ *A61F 9/0084* (2013.01); *A61F 9/00827* (2013.01); *A61F 9/00838* (2013.01);
(Continued)

(58) Field of Classification Search
CPC .... A61F 9/008; A61F 9/0084; A61F 9/00827; A61F 9/00838; A61F 2009/0087;
(Continued)

(56) References Cited

U.S. PATENT DOCUMENTS 7,173,745 B2 * 2/2007 Dair .................... A61F 9/00804
                                                          359/196.1
2013/0150837 A1 * 6/2013 Rathjen .................. A61F 9/008
                                                          606/4

FOREIGN PATENT DOCUMENTS

WO    2011/016999 A2    2/2011
WO    2015/078803 A1    6/2015
(Continued)

OTHER PUBLICATIONS

Icnirp, "Revision of Guidelines on Limits of Exposure to Laser Radiation of Wavelenghts Between 400 nm and 1.4 μm". Health Physics 79(4): 431-440; 2000.

*Primary Examiner* — Nathan J Jenness
(74) *Attorney, Agent, or Firm* — BCF LLP (57) ABSTRACT

The invention relates to a treatment apparatus including a device for conditioning a LASER beam generated by a femtosecond laser, the conditioning device comprising an optical sweeping scanner (30) and a focusing optical system (40) downstream of the optical sweeping scanner (30), remarkable in that a pivoting mirror (32) of the optical sweeping scanner (30) is positioned between an object focal plane $F_{object}$ of the focusing optical system (40) and the focusing system (40).

6 Claims, 5 Drawing Sheets

(52) U.S. Cl.
CPC .............. *A61F 2009/0087* (2013.01); *A61F 2009/00872* (2013.01); *A61F 2009/00887* (2013.01); *A61F 2009/00897* (2013.01)

(58) Field of Classification Search
CPC .. A61F 2009/00872; A61F 2009/00887; A61F 2009/00897
See application file for complete search history.

(56) References Cited

FOREIGN PATENT DOCUMENTS

| WO | 2015/178803 | A1 | | 11/2015 | |
|---|---|---|---|---|---|
| WO | WO2015/178803 | A1 | * | 11/2015 | ............. A61F 9/008 |
| WO | 2017/016999 | A1 | | 2/2017 | |
| WO | 2017/174710 | A1 | | 10/2017 | |

* cited by examiner

APPARATUS FOR TREATING A TISSUE, INCLUDING ORIGINAL OPTICAL SYSTEMS OF DEFLECTION AND FOCUSING OF A LASER BEAM

CROSS-REFERENCE TO RELATED APPLICATIONS

This application is a national phase filing under 35 U.S.C. § 371 of International Application No. PCT/EP2019/058627 filed on Apr. 5, 2019, which claims benefit of priority from French Patent Application No. 1870407 filed Apr. 6, 2018, the contents of which are hereby incorporated by reference in their entirety.

TECHNICAL FIELD

The present invention relates to the technical field of surgical operations performed with femtosecond laser, and more particularly to that of ophthalmological surgery in particular for applications of cutting corneas or crystalline lenses.

The invention relates to a device for cutting a human or animal tissue, such as a cornea or a crystalline lens by means of a femtosecond laser.

By femtosecond laser is meant a light source able to emit a laser beam in the form of ultra-short pulses, whose duration is comprised between 1 femtosecond and 100 picoseconds, preferably comprised between 1 and 1,000 femtoseconds, in particular around one hundred femtoseconds.

PRIOR ART

The femtosecond lasers are commonly used in surgery for cutting the cornea or the crystalline lens. They deliver ultra-short and high-power pulses.

During a surgery on the cornea, the femtosecond laser can be used to make a cutting of the corneal tissue, by focusing a laser beam in the stroma of the cornea. More specifically, at each pulse, the femtosecond laser generates a beam. This beam is focused (at a point called located "focusing" point) in the cornea. A gas bubble is formed at the focusing point, causing a very localized disruption of the surrounding tissues. Part of the beam energy is consumed during the generation of the gas bubble. The rest of the beam energy propagates up to the retina, causing a local heating of the retina.

In order to form a cutting line in the cornea, a succession of small adjacent gas bubbles are generated by moving the beam. In order to move the beam, a sweeping scanner 1 is used. This sweeping scanner 1 is generally composed of controllable galvanometer mirrors and/or of plates allowing the displacement of optical elements, such as mirrors.

Figure 1:
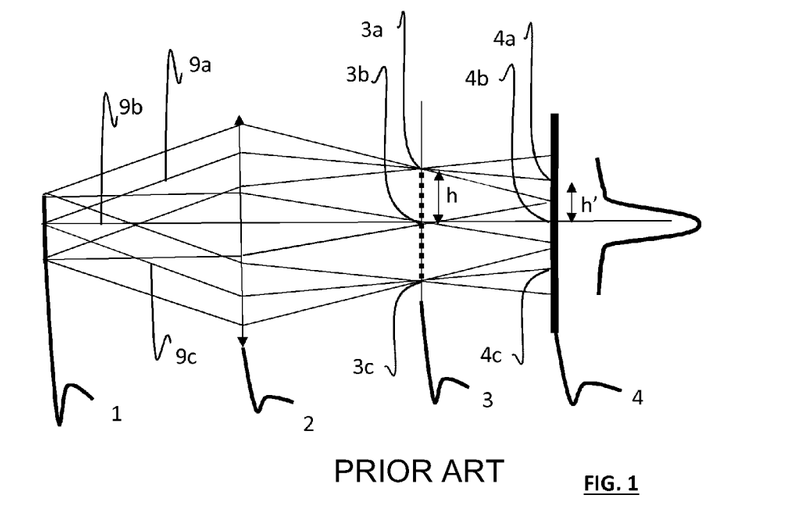
FIG. 1 is a schematic representation of an example of a device for treating an ocular pathology using a femtosecond laser.

Referring to FIG. 1, at each pulse, the beam derived from the femtosecond laser:
- enters the sweeping scanner 1,
- passes through a focusing assembly 2,
- focuses at a focusing point in the cornea 3 to form a gas bubble, then
- diverges towards the retina 4 of the patient.

This divergence of the beam tends to heat the retina 4.

To reduce the risks of degradation of the retina 4 upon exposure to a beam generated by a femtosecond laser, limit irradiances have been calculated for a patient's eye as a function of time. The document entitled "ICNIRP Guidelines on limits of exposure to laser radiation of wavelengths between 180 nm AND 1,000 mm" from "International Commission on Non-Ionizing Radiation Protection" describes such limit irradiances as a function of the laser emission wavelength(s) and of the duration of exposure to the beam generated by the femtosecond laser (see in particular tables 5 and 6 of this document).

Figure 2:
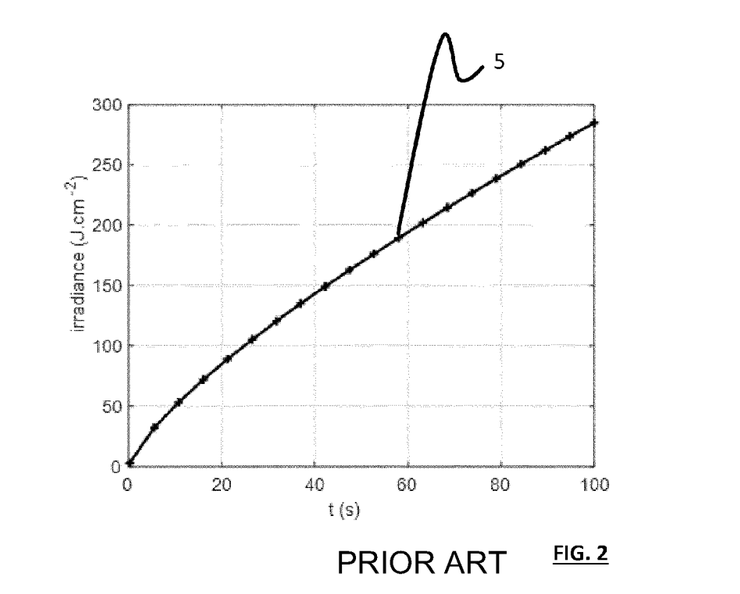
FIG. 2 is a schematic representation of a limit irradiance curve as a function of time.

By way of indication, a curve 5 illustrating the limit radiant exposures (expressed in Joules/cm$^2$) as a function of time is represented in FIG. 2.

When using a femtosecond laser in the treatment of an ocular pathology, it is necessary that the radiant exposure of the retina (for a given retinal exposure time) is less than a limit radiant exposure defined by the curve illustrated in FIG. 2. This allows guaranteeing the integrity of the retina when using the femtosecond laser in the treatment of the ocular pathology.

To cut a cornea on a surface of 1 mm$^2$, it is necessary to achieve about 20,000 impacts very close to each other. These impacts are achieved one by one at an average speed of 300,000 impacts/second. To cut a cornea on a surface of about 65 mm$^2$, taking into account the times during which the laser stops producing pulses at the end of the segment to allow the mirrors to be positioned on the next segment, it takes an average of 15 seconds. The surgical cutting operation is therefore slow.

To optimize the cutting time, it is known to increase the frequency of the laser. However, the increase of the frequency also implies an increase of the speed of displacement of the beam, by means of suitable plates or scanners. It is also known to increase the spacing between the impacts of the laser on the tissue to be cut, but generally at the expense of the cutting quality.

Another solution for reducing the cutting time consists in generating several gas bubbles simultaneously. The fact of simultaneously generating "n" gas bubbles allows reducing the total duration of the cutting by a factor greater than "n" (because the number of round trips that the beam must perform to treat a whole surface of the tissue is also reduced).

Generating a plurality of gas bubbles simultaneously requires increasing the power of the femtosecond laser such that at each focusing point, the power derived from the femtosecond laser is sufficient to generate a respective gas bubble.

This increase in power induces an increase in the radiant exposure received by the retina, which can then exceed the limit radiant exposures given by the document "ICNIRP Guidelines on limits of exposure to laser radiation of wavelengths between 180 nm AND 1,000 mm" from "International Commission on No-Ionizing Radiation Protection".

An aim of the present invention is to propose a device for treating an ocular pathology including a high-power femtosecond laser and which allows complying with the constraints related to the limit radiant exposures that a retina can withstand.

DISCLOSURE OF THE INVENTION

To this end, the invention proposes an apparatus for treating a human or animal tissue, such as a cornea or a crystalline lens, said apparatus including a device for conditioning a laser beam generated by a femtosecond laser, the conditioning device being disposed downstream of the femtosecond laser and comprising an optical scanner and a focusing optical system downstream of the optical sweeping scanner:

the optical sweeping scanner including at least one optical mirror pivoting around at least one axis to deflect the laser beam, the focusing optical system including a concentrator module to focus the laser beam in a focusing plane, remarkable in that said at least one pivoting optical mirror of the optical sweeping scanner is positioned between an object focal plane $F_{object}$ of the focusing optical system and the focusing system.

Preferred but non-limiting aspects of the apparatus according to the invention are as follows:

said and at least one pivoting optical mirror of the optical sweeping scanner extends over the optical path of the laser beam between:
the object focal plane $F_{object}$ of an equivalent lens corresponding to the focusing optical system, and
an input orifice of the focusing optical system;
an entrance pupil of the concentrator module is positioned in the plane of the equivalent lens corresponding to the focusing optical system;
the focusing optical system includes an optical relay device upstream of the concentrator module;
the optical relay device is positioned along the optical path of the laser beam so as to form an image of an area in the vicinity of said at least one pivoting optical mirror in the plane of the equivalent lens corresponding to the focusing optical system;
the conditioning device further comprises a beam shaping system, to modulate the phase of the wavefront of the laser beam so as to obtain a phase-modulated laser beam according to a modulation setpoint calculated to distribute the energy of the laser beam into at least two points of impact forming a pattern in the focusing plane;
the conditioning device further comprises a control unit for driving the femtosecond laser, the optical sweeping scanner and the focusing optical system;
the concentrator module can be movable in translation along the optical path of the laser beam between first and second extreme positions, the concentrator module being closer to the optical relay device in the first extreme position than in the second extreme position;
the cutting apparatus may further comprise a pre-compensatory optical device positioned upstream of the focusing optical system so as to generate a compensatory aberration at the output of the focusing optical system, said compensatory aberration making it possible to compensate for the aberrations produced on the laser beam in particular by the passage through the human or animal tissue, the control unit being adapted to control the translational displacement of the concentrator module as a function of the distance estimated by the calculator.

BRIEF DESCRIPTION OF THE DRAWINGS

Other characteristics and advantages of the invention will clearly emerge from the description given below, by way of indication and without limitation, with reference to the appended figures, in which.

DETAILED DISCLOSURE OF THE INVENTION

The invention relates to an apparatus for treating an ocular pathology. More specifically, the invention relates to an apparatus for cutting a human tissue by means of a femtosecond laser. In the remainder of the description, the invention will be described, by way of example, for the cutting of a cornea of a human or animal eye.

1. Definitions

In the context of the present invention, it is meant by the term "point of impact" an area of the laser beam comprised in its focal plane in which the intensity of said laser beam is sufficient to generate a gas bubble in a tissue.

In the context of the present invention, it is meant by "adjacent points of impact" two points of impact disposed facing each other and not separated by another point of impact. It is meant by "neighboring points of impact" two points in a group of adjacent points between which the distance is minimum.

In the context of the present invention, it is meant by "pattern" a plurality of laser points of impact generated simultaneously in a focusing plane of a shaped, that is to say phase-modulated, laser beam to distribute its energy into several distinct spots in the focusing plane corresponding to the cutting plane of the device.

2. Cutting Apparatus

Figure 3:
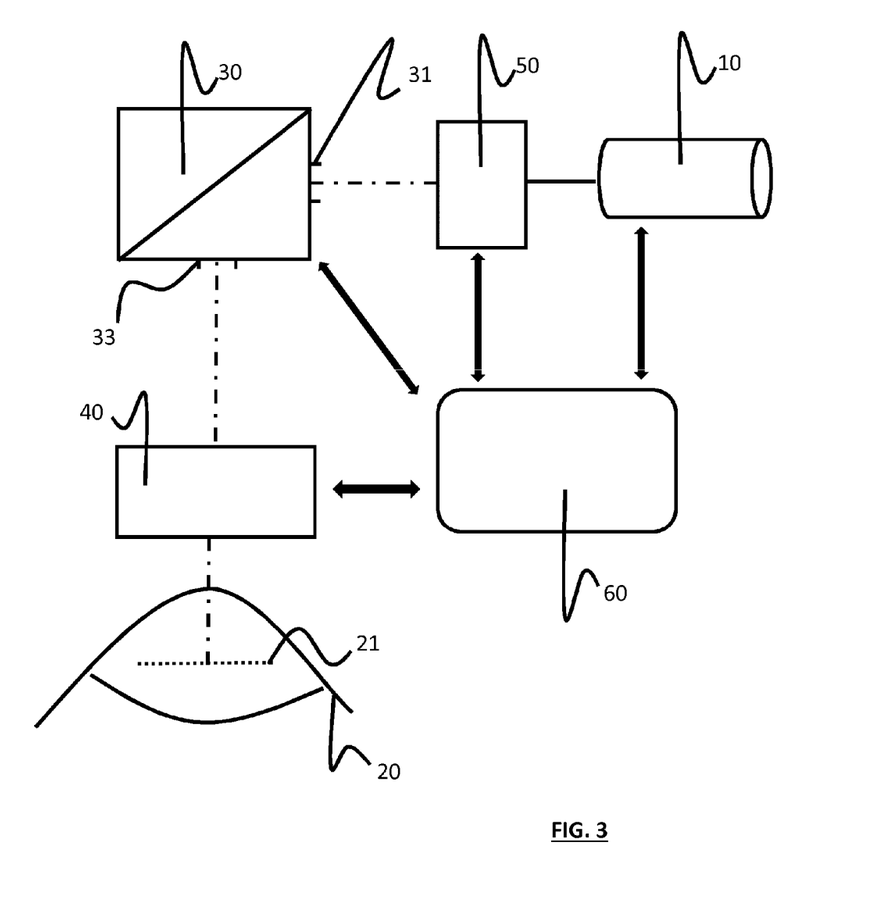
FIG. 3 is a schematic representation of a mounting including the cutting apparatus according to the invention.
Figure 4:
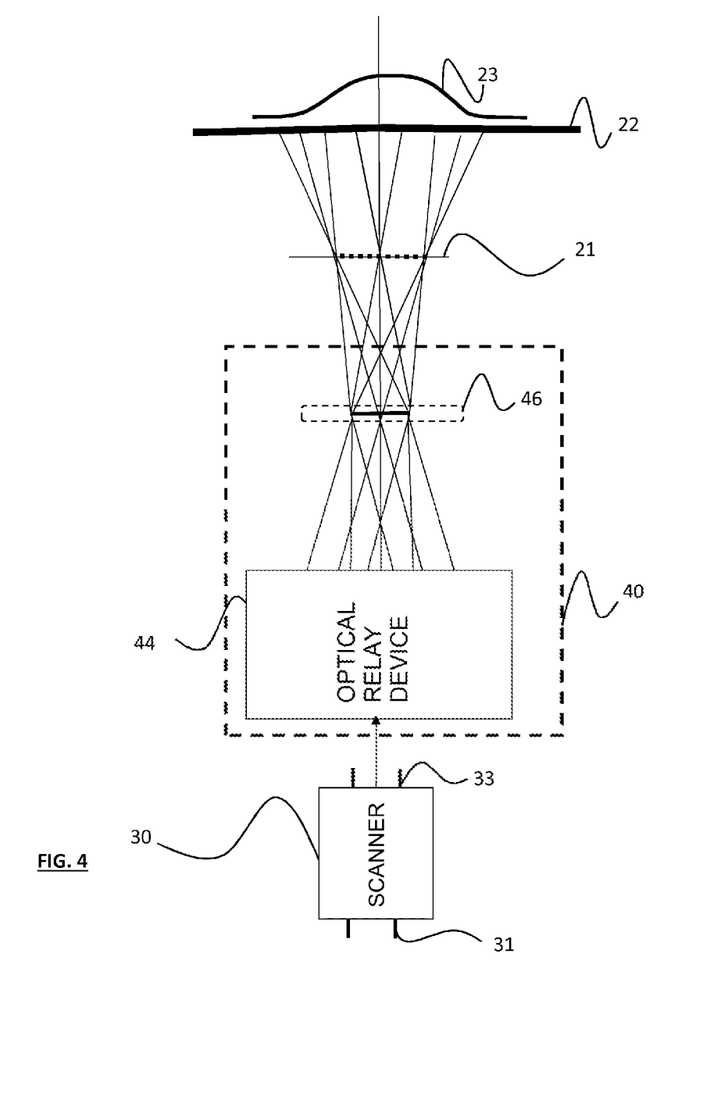
FIGS. 4 to 6 are schematic representations of an optical sweeping scanner and a focusing optical system of the cutting apparatus according to the invention.

FIG. 3 illustrates an embodiment of the cutting apparatus according to the invention. This can be disposed between a femtosecond laser 10 and a target to be treated 20.

The femtosecond laser 10 is able to emit a laser beam in the form of pulses. For example, the laser 10 emits a light of 1030 nm in wavelength, in the form of 400-femtosecond pulses. The laser 10 has a power of 20 W and a frequency of 500 kHz.

The target 20 is, for example, a human or animal tissue to be cut such as a cornea or a crystalline lens.

The cutting apparatus comprises a beam conditioning device including:
an optical sweeping scanner 30 downstream of the laser 10,
a focusing optical system 40 downstream of the optical sweeping scanner 30.

The conditioning device also includes a control unit 60 for driving the optical sweeping scanner 30 and the focusing optical system 40.

The optical scanner 30 allows orienting the beam derived from the laser 10 to move it along a path of displacement predefined by the user in a focusing plane 21.

Figure 5:
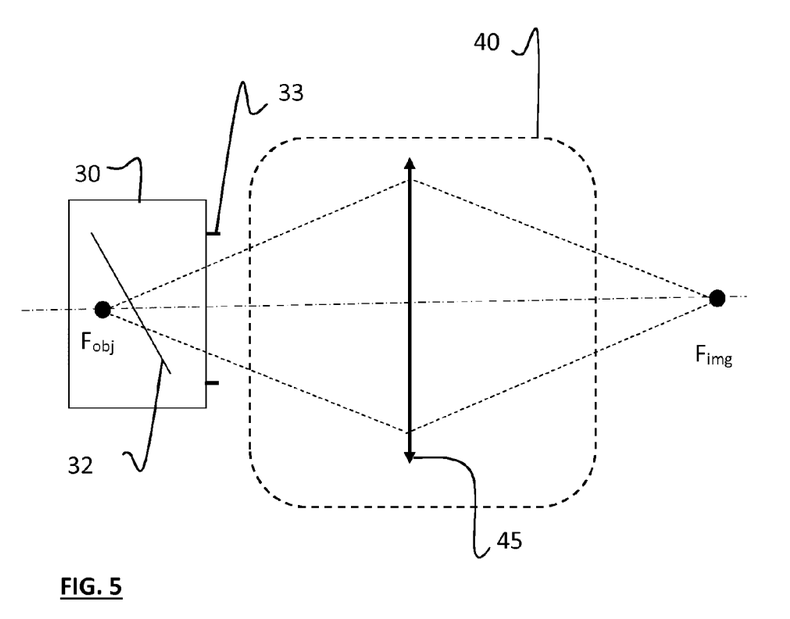

The focusing optical system 40 allows focusing the beam in the focusing plane 21—corresponding to the cutting plane. As an indication, FIG. 5 illustrates an equivalent lens 45 corresponding to the focusing optical system 40 as a whole, being well understood by those skilled in the art that the focusing optical system is not just a fixed lens.

The conditioning device may also include a shaping system 50 between the femtosecond laser 10 and the optical sweeping scanner 30. This shaping system 50 is positioned on the path of the beam derived from the femtosecond laser 10. The shaping system 50 allows modulating the phase of the beam derived from the femtosecond laser 10 in order to distribute the energy of the beam into a plurality of points of impact in its focal plane, this plurality of points of impact defining a pattern.

Thus, the shaping system 50 allows simultaneously generating several points of impact defining a pattern, the optical scanner 30 allows moving this pattern in the focusing plane 21, and the focusing optical system 40 allows focusing the beam in the focusing plane 21.

The various elements constituting the conditioning device will now be described in more detail with reference to the figures.

3. Elements of the Conditioning Device 3.1. Optical Sweeping Scanner

The optical sweeping scanner 30 allows deflecting the beam (possibly phase-modulated beam) so as to move it into a plurality of positions in the focusing plane 21 corresponding to the cutting plane.

The optical sweeping scanner 30 comprises:
- an input orifice 31 to receive the beam (possibly phase-modulated by the shaping unit 50),
- one (or several) optical mirror(s) 32 pivoting around one (or several) axis/axes to deflect the laser beam, and
- an output orifice 33 to send the laser beam to the focusing optical system 40.

The optical scanner 30 used is for example a scanning head of the IntelliScan III series from the SCANLAB AG company. The mirror(s) 32 of the optical scanner is/are connected to one (or several) motor(s) to allow it/them to pivot. This/these motor(s) for the pivoting of the mirror(s) 32 is/are advantageously driven by the unit of the control unit 60 which will be described in more detail below.

Advantageously, and as illustrated in FIG. 5, the pivoting optical mirror(s) 32 of the optical sweeping scanner 30 is/are positioned between an object focal plane $F_{object}$ of the focusing optical system 40 and the focusing system 40. This allows increasing the scanning angle at the output of the focusing system 40 so that the energy emitted by the femtosecond laser is distributed over a larger surface of the retina.

It is thus possible to increase the power of the femtosecond laser 10 while maintaining the irradiance received by the retina in a range of value lower than the limit irradiances given by the document "ICNIRP Guidelines on limits of exposure to laser radiation of wavelengths between 180 nm AND 1,000 mm" from "International Commission on Non-Ionizing Radiation Protection".

The control unit 60 is programmed to drive the optical sweeping scanner 30 so as to move the pattern along a path of displacement contained in the focusing plane.

3.2. Focusing Optical System

The focusing optical system 40 allows focusing the beam in a cutting plane.

The focusing optical system 40 may include:
- an input orifice 41 to receive the deflected beam derived from the optical sweeping scanner 30,
- a concentrator module 46 to focus the laser beam in the focusing plane 21 and
- an output orifice 43 to send the focused beam to the tissue to be treated.

The focusing optical system may also comprise a depth positioning module to move the focusing plane.

Figure 6:
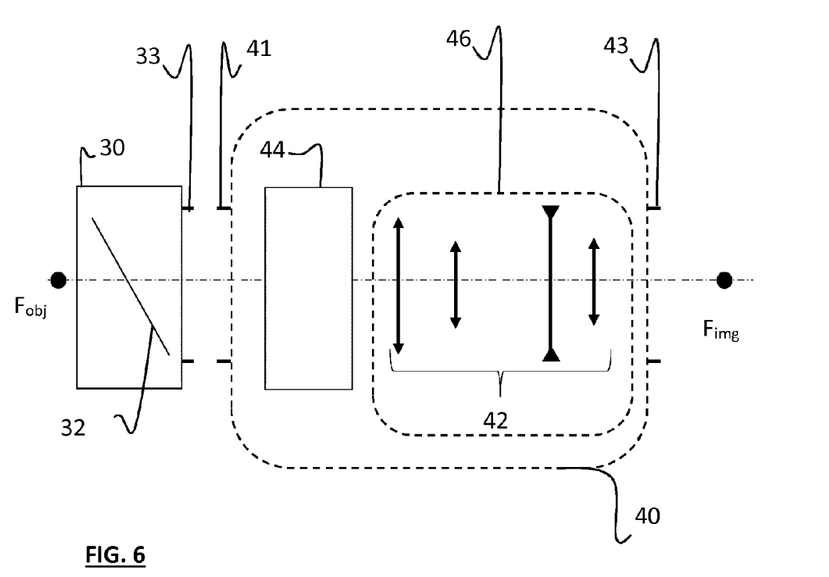

For example with reference to FIG. 6, the concentrator module 46 comprises a plurality of (converging and/or diverging) lenses 42 and the depth positioning module comprises one (or several) motor(s) (not represented) associated to one (or several) lens(es) 42 of the concentrator module 46 to allow its/their translational displacement along the optical path of the beam in order to vary the depth of the focusing plane.

As a variant, the focusing optical system can be devoid of a depth positioning module. The modification of the position of the focusing plane can then be obtained by modifying the divergence of the beam upstream of the focusing optical system or by moving in depth the cutting apparatus (or the conditioning device) in front of the target tissue to be treated.

The concentrator module 46 is optically defined by:
- an aperture diaphragm (i.e. element of the concentrator module 46 which most limits the passage of the beam: it can be a mechanical diaphragm or limits of one of the lenses of the concentrator module 46),
- an entrance pupil (i.e. image of the aperture diaphragm through the part of the concentrator module 46 located upstream of the aperture diaphragm along the optical path of the beam),
- an exit pupil (i.e. image of the aperture diaphragm through the part of the concentrator module 46 located downstream of the aperture diaphragm along the optical path of the beam).

The entrance pupil of the concentrator module 46 can be positioned in the plane of the equivalent lens 45 of the focusing optical system 40. This allows, on the one hand, spreading the remaining energy over a larger surface of the retina and, on the other hand, facilitating the optimization of the cutting device according to the invention.

The focusing optical system 40 may also comprise an optical relay device 44 (relay lens) forming an entrance pupil transport device. The optical relay device 44 allows imaging an area in the vicinity of the optical mirror(s) 32 of the optical sweeping scanner 30 on the entrance pupil of the concentrator module 46. This area may correspond to the middle of the optical mirror(s) 32 (i.e. the structural center of the optical mirror(s) 32).

The optical relay device 44 consists of a plurality of lenses (for example convex lenses). Such an optical relay device 44 is known to those skilled in the art and will not be described in more detail below.

The control unit 60 is programmed to drive the displacement of the lens(es) of the focusing optical system 40 along an optical path of the beam so as to move it in the focusing plane 21 in at least three respective cutting planes so as to form a stack of cutting planes of the tissue 20. This allows performing a cutting in a volume, for example as part of a refractive surgery.

Advantageously, the concentrator module 46 can be movable in translation along the optical path of the laser beam between first and second extreme positions, the concentrator module 46 being closer to the optical relay device 44 in the first extreme position than in the second extreme position. This allows adjusting the depth of the focusing plane corresponding to the cutting plane.

The cutting device may also comprise a pre-compensatory optical system—integrating for example lenses, some of which are movable—positioned upstream of the focusing optical system. This pre-compensatory optical system allows generating a compensatory aberration at the output of the focusing optical system 40.

Indeed, when the laser beam derived from the cutting device passes through:
- a coupling interface (as described for example in the document) positioned between the cutting device and the patient's eye, and
- the tissues (cornea and crystalline lens) of the patient's eye, the laser beam undergoes deformations inducing the formation of aberrations.

The integration of a pre-compensatory optical system allows correcting these aberrations undergone by the laser beam. The arrangement of the pre-compensatory optical system—and particularly the positions of the mobile lenses of the pre-compensatory optical system—can be determined by a calculator as a function of the desired compensatory aberration by using any technique known to those skilled in the art.

3.3. Shaping System

The spatial beam-shaping system 50 allows varying the wavefront of the beam to achieve points of impact separated from each other in the focal plane.

More specifically, the shaping system 50 allows modulating the phase of the beam derived from the femtosecond laser 10 to form intensity peaks in the focal plane of the beam, each intensity peak producing a respective point of impact in the focal plane corresponding to the cutting plane. The shaping system 50 is, according to the illustrated embodiment, a liquid-crystal Spatial Light Modulator, known by the acronym SLM.

The SLM allows modulating the final beam energy distribution, in particular in the focal plane 21 corresponding to the cutting plane. More specifically, the SLM is adapted to modify the spatial profile of the wavefront of the primary beam derived from the femtosecond laser 10 to distribute the energy of the laser beam in different focusing spots in the focusing plane.

The phase-modulation of the wavefront can be seen as a phenomenon of two-dimensional interferences. Each portion of the primary beam derived from the femtosecond laser 10 is delayed or advanced relative to the initial wavefront so that each of these portions is redirected so as to perform constructive interference at N distinct points in the focal plane of a lens. This redistribution of energy into a plurality of points of impact only takes place in a single plane (i.e. the focusing plane) and not throughout the propagation path of the modulated beam. Thus, the observation of the modulated beam before or after the focusing plane does not allow identifying a redistribution of the energy into a plurality of distinct points of impact, because of this phenomenon which can be likened to constructive interferences (which take place only in a plane and not throughout the propagation as in the case of the separation of a primary beam into a plurality of secondary beams).

The SLM is a device made up of an orientation-controlled liquid-crystal layer that allows dynamically shaping the wavefront, and therefore the phase of the beam. The liquid-crystal layer of an SLM is organized as a grid (or matrix) of pixels. The optical thickness of each pixel is electrically controlled by orientation of the liquid crystal molecules belonging to the surface corresponding to the pixel. The SLM uses the anisotropic principle of the liquid crystals, that is to say the modification of the index of the liquid crystals, depending on their spatial orientation. The orientation of the liquid crystals can be achieved using an electric field. Thus, the modification of the liquid-crystal index changes the wavefront of the laser beam.

In a known manner, the SLM implements a phase mask, that is to say a map determining how the phase of the beam must be modified to obtain a given amplitude distribution in its focusing plane. The phase mask is a two-dimensional image whose each point is associated with a respective pixel of the SLM. This phase mask allows driving the index of each liquid-crystal of the SLM by converting the value associated with each point of the mask—represented in gray levels comprised between 0 and 255 (therefore from black to white)—into a control value—represented in a phase comprised between 0 and 2n. Thus, the phase mask is a modulation setpoint displayed on the SLM to drive in reflection an unequal spatial phase shift of the primary beam illuminating the SLM. Of course, those skilled in the art will appreciate that the gray level range may vary depending on the model of SLM used. For example, in some cases, the gray level range can be comprised between 0 and 220. The phase mask is generally calculated by an iterative algorithm based on the Fourier transform, or on various optimization algorithms, such as genetic algorithms, or the simulated annealing. Different phase masks can be applied to SLMs as a function of the number and position of the desired points of impact in the focal plane of the beam. In any case, those skilled in the art know how to calculate a value at each point of the phase mask to distribute the energy of the beam into different focusing spots in the focal plane.

The SLM therefore allows generating, from a Gaussian laser beam, a single point of impact, and by means of the phase mask, distributing its energy by phase modulation so as to simultaneously generate several points of impact in its focusing plane from a single laser beam shaped by phase modulation (a single beam upstream and downstream of the SLM).

In addition to a reduction in the cornea cutting time, the technique of modulation of the laser beam phase allows other improvements, such as a better surface quality after cutting or a reduction in the endothelial mortality. The different points of impact of the pattern can, for example, be evenly spaced over the two dimensions of the focal plane of the laser beam, so as to form a grid of laser spots.

The use of a pupil relay system induces the formation of an intermediate focus in the path of the beam. For the femtosecond laser pulses, this can lead to an intensity at the intermediate focus such that non-linear effects occur at the focal point of the type Kerr effect or plasma breakdown and generation. This then results in a degradation of the optical quality of the beam. Therefore, an optical configuration should be selected, in which the size of the beam at the intermediate focus allows maintaining the intensity low enough not to generate these effects.

In this sense, the use of a beam-shaping device has the effect of distributing the energy over "n" points in the focusing plane. The intensity is therefore divided by "n" relative to a non-shaped beam. The shaping of the beam therefore allows conveying more energy in the same beam without generating non-linear effects.

3.4. Control Unit

As indicated above, the control unit 60 allows controlling the various elements constituting the cutting apparatus, namely the femtosecond laser 10, the optical sweeping scanner 30 and the focusing optical system 40 and the shaping system 50.

The control unit 60 is connected to these different elements via one (or several) communication bus(es) allowing:
the transmission of control signals such as
the phase mask at the shaping system,
the activation signal at the femtosecond laser,
the scanning speed at the optical sweeping scanner 30,
the position of the optical sweeping scanner 30 along the displacement path,
the cutting depth at the focusing optical system.
the receipt of measurement data derived from the various elements of the system such as
the scanning speed reached by the optical scanner 30, or
the position of the focusing optical system, etc.;

The control unit 60 may consist of one (or several) workstation(s) and/or one (or several) computer(s) or may be of any other type known to those skilled in the art. The control unit 60 may for example comprise a mobile phone, an electronic tablet (such as an IPAD®)), a Personal Digital Assistant (or PDA), etc. In all cases, the control unit 60 comprises a processor programmed to allow the driving of the femtosecond laser 10, the optical sweeping scanner 30, the focusing optical system 40, the shaping system 50, etc.

4. Theory Relating to the Invention and Advantages in Relation to the Devices of the Prior Art The cutting apparatus described above allows treating a cataract by focusing of a laser beam in different areas of the crystalline lens so as to fragment it into pieces small enough to be aspirated by an irrigation-aspiration probe.

The focusing of the beam derived from the femtosecond laser is made by means of a beam processing device located between the femtosecond laser and the patient's eye.

The beam derived from the femtosecond laser is composed of a succession of time pulses. From pulse to pulse, the focal point is moved in the crystalline lens so as to generate a succession of impacts. The displacement of the focal point is achieved by deflection of the beam by means of the deflection optical system.

For each pulse, part of the pulse energy is consumed by vaporization of the tissue. The rest of the energy is absorbed by the retina, which locally causes its heating.

A large number of pulses are required to cut the crystalline lens. The total energy absorbed by the retina and the heating resulting therefrom represents a limit for the femtosecond laser processing technology.

A beam processing device of the prior art is represented in FIG. 1. This processing device comprises a sweeping scanner 1 and a focusing assembly 2. The mirrors of the sweeping scanner are placed on either side and equidistant from a first position corresponding to the entrance pupil of the focusing assembly 2.

For a mirror at position 0, the ray 9b is parallel to the optical axis of the focusing assembly 2. It is focused by the focusing assembly 2 in the image focal plane 3 located in the crystalline lens. Part of the energy of the focused beam generates damage at point 3b. The remaining energy continues to propagate along the optical axis and meets the retina around the point 4b. The size of the beam is then enlarged due to the divergence of the beam resulting from the focusing.

For a mirror in maximum angular position, the ray is deflected from the optical axis along the path 9a. It is focused by the focusing assembly 2 at point 3a of the crystalline lens, at a distance h from the center. The remaining energy meets the retina around the point 4a located at a distance h' from the center of the retina.

Likewise, for a mirror in minimum angular position, the ray is deflected from the optical axis along the path 9c. It is focused by the focusing assembly 2 at the point 3c of the crystalline lens. The remaining energy meets the retina around the point 4c.

In the beam processing devices currently used for the cataract surgery, the angle made by the rays at the output of the processing device is such that the beam tends to approach the optical axis with the propagation. This is due to the position of the scanner mirrors that are located before the object focus of the focusing assembly 2. Thus, the distance h' is smaller than the distance h: the surface on which the energy is distributed over the retina is therefore smaller than the surface scanned by the crystalline lens. The total energy that can be sent into the crystalline lens is limited by this low spreading.

In the context of the present invention, the mirrors of the optical sweeping scanner 32 are positioned on the optical path after the object focal point $F_{object}$ of the focusing optical system 40. In this configuration, the beam moves away from the optical axis at the output of the focusing optical system 40. A greater spreading 23 of the energy over the retina 22 is then obtained, which leads to a lower temperature rise. This has the effect of pushing the limits of the total cumulative energy used during surgery.

This spreading effect is all the more important as the position of the scanner is away from the object focus $F_{object}$. The entrance pupil of the focusing optical system 40 can for example be placed in the plane of the equivalent lens 45 of the focusing optical system 40.

Such a configuration can for example be made by using a pupil relay device placed so as to image the middle of the mirrors of the scanner in the plane of the equivalent lens 45 corresponding to the focusing optical system 40.

5. Conclusions

Thus, the invention allows disposing an efficient cutting tool.

The positioning of the pivoting optical mirror(s) of the optical sweeping scanner 30 between the object focal plane $F_{object}$ of the focusing optical system 40 and the focusing system 40 allows a greater spreading of the energy over the retina, and therefore a lower temperature rise.

It is thus possible to increase the power of the femtosecond laser 10 without exceeding the limit irradiances likely to degrade the retina.

The invention has been described for operations of cutting a cornea in the field of the ophthalmological surgery, but it is obvious that it can be used for other types of operations in ophthalmological surgery without departing from the context of the invention. For example, the invention finds application in the corneal refractive surgery, such as the treatment of ametropia, in particular myopia, hypermetropia, astigmatism, in the treatment of loss of accommodation, in particular presbyopia. The invention also finds application in the treatment of the cataract with incision of the cornea, cutting of the anterior capsule of the crystalline lens and fragmentation of the crystalline lens. Finally, more generally, the invention relates to all clinical or experimental applications on the cornea or the crystalline lens of a human or animal eye. Even more generally, the invention relates to the broad field of laser surgery and finds advantageous application when it comes to vaporizing human or animal soft tissues with high water content.

The reader will understand that many modifications can be made to the invention described above without materially departing from the novel teachings and advantages described here.

Consequently, all modifications of this type are intended to be incorporated within the scope of the appended claims.

The invention claimed is:

1. An apparatus for treating a human or animal tissue, said apparatus including a conditioning device for conditioning a laser beam generated by a femtosecond laser, the conditioning device being disposed downstream of the femtosecond laser and comprising an optical sweeping scanner and a focusing optical system downstream of the optical sweeping scanner:

the optical sweeping scanner including at least one optical mirror pivoting around at least one axis to deflect the laser beam, the focusing optical system including a concentrator module to focus the laser beam in a focusing plane and an optical relay device upstream of the concentrator module, wherein said at least one pivoting optical mirror of the optical sweeping scanner extends over an optical path of the laser beam between:

an object focal plane ($F_{object}$) of an equivalent lens corresponding to an imaginary lens having the same equivalent focal length as the focusing optical system as a whole, and an input orifice of the focusing optical system.

2. The treatment apparatus according to claim 1, wherein an entrance pupil of the concentrator module is positioned in a plane including the equivalent lens corresponding to the focusing optical system as a whole.

3. The treatment apparatus according to claim 1, wherein the optical relay device is positioned along the optical path of the laser beam so as to form an image of an area in the vicinity of said at least one pivoting mirror in a plane including the equivalent lens corresponding to the focusing optical system.

4. The treatment apparatus according to claim 1, wherein the conditioning device further comprises a beam shaping system to modulate the phase of the wavefront of the laser beam so as to obtain a phase-modulated laser beam according to a modulation setpoint calculated to distribute the energy of the laser beam into at least two points of impact forming a pattern in the focusing plane.

5. The treatment apparatus according to claim 1, wherein the conditioning device further comprises a control unit for driving the femtosecond laser, the optical sweeping scanner and the focusing optical system.

6. The treatment apparatus according to claim 1, wherein the concentrator module is movable in translation along the optical path of the laser beam between first and second extreme positions, the concentrator module being closer to the optical relay device in the first extreme position than in the second extreme position.

* * * * *